(12) United States Patent
Li et al.

(10) Patent No.: US 7,658,541 B2
(45) Date of Patent: Feb. 9, 2010

(54) APPARATUS FOR UNIVERSAL ELECTROMAGNETIC NAVIGATION TARGET FOR FLUOROSCOPIC SYSTEMS

(75) Inventors: Dun Alex Li, Salem, NH (US); Richard Aufrichtig, Palo Alto, CA (US); Lonnie B. Weston, Syracuse, NY (US); Peter Traneus Anderson, Andover, MA (US)

(73) Assignee: General Electric Company, Schenectady, NY (US)

( * ) Notice: Subject to any disclaimer, the term of this patent is extended or adjusted under 35 U.S.C. 154(b) by 321 days.

(21) Appl. No.: 11/768,578

(22) Filed: Jun. 26, 2007

(65) Prior Publication Data

US 2009/0002968 A1 Jan. 1, 2009

(51) Int. Cl.
*H05G 1/00* (2006.01)
(52) U.S. Cl. .................... 378/204; 378/207
(58) Field of Classification Search ............. 378/154, 378/185, 186, 189, 204, 207
See application file for complete search history.

(56) References Cited

U.S. PATENT DOCUMENTS

| | | | |
|---|---|---|---|
| 5,635,714 A | 6/1997 | Nablo et al. | |
| 6,246,231 B1 | 6/2001 | Ashe | |
| 6,490,475 B1 | 12/2002 | Seeley et al. | |
| 6,636,757 B1 | 10/2003 | Jascob et al. | |
| 7,075,088 B2 * | 7/2006 | Watanabe et al. | 250/370.01 |
| 7,096,148 B2 | 8/2006 | Anderson et al. | |
| 2004/0097805 A1 | 5/2004 | Verard et al. | |
| 2006/0098851 A1 * | 5/2006 | Shoham et al. | 382/128 |
| 2008/0224056 A1 * | 9/2008 | Liu et al. | 250/370.09 |

FOREIGN PATENT DOCUMENTS

| | | |
|---|---|---|
| JP | 2005274379 | 6/2005 |
| JP | 2005274379 A | 10/2005 |

OTHER PUBLICATIONS

V. V. Kindratenko, "A survey of electromagnetic position tracker calibration techniques", Virtual Reality: Research, Development, and Applications, pp. 169-182, vol. 5, No. 3, 2000.
GB International Search Report Application No. GB0811107.2 (7 pages) Oct. 28, 2008 and Mar. 18, 2009.

* cited by examiner

*Primary Examiner*—Jurie Yun
(74) *Attorney, Agent, or Firm*—McAndrews, Held & Malloy, Ltd.; Peter J. Vogel; Michael A. Dellapenna

(57) ABSTRACT

Certain embodiments of the present invention provide a system for an electromagnetic shield assembly for use with C-arms. In an embodiment, the system may include a ring shield configured to encompass an x-ray detector. The ring shield may have a first window opening to receive x-rays. The system may also include a window shield configured to shield the first window opening of the ring shield. Certain embodiments of the present invention may provide a system for a universal navigation target. In an embodiment, the system may include a radiolucent calibration target and an electromagnetic shield. The electromagnetic shield may include a ring shield having a first window opening to receive x-rays and a window shield configured to shield the first window opening of the ring shield.

20 Claims, 3 Drawing Sheets

APPARATUS FOR UNIVERSAL ELECTROMAGNETIC NAVIGATION TARGET FOR FLUOROSCOPIC SYSTEMS

BACKGROUND OF THE INVENTION

The present invention generally relates to a system and method for improving the accuracy of an electromagnetic navigation system for use with medical applications. Particularly, the present invention relates to a system and method for improving the effectiveness of an electromagnetic shield assembly for use on a C-arm.

Electromagnetic type navigation systems are useful in numerous applications. One application of particular use is in medical applications, and more specifically, image guided surgery. Typical image guided surgical systems acquire a set of images of an operative region of a patient's body and track a surgical tool or instrument in relation to one or more sets of coordinates. At the present time, such systems have been developed or proposed for a number of surgical procedures such as brain surgery and arthroscopic procedures on the knee, wrist, shoulder or spine, as well as certain types of angiography, cardiac or other interventional radiological procedures and biopsies. Such procedures may also involve preoperative or intraoperative x-ray images being taken to correct the position or otherwise navigate a tool or instrument involved in the procedure in relation to anatomical features of interest. For example, such tracking may be useful for the placement of an elongated probe, radiation needle, fastener or other article in tissue or bone that is internal or is otherwise positioned so that it is difficult to view directly.

An electromagnetic tracking system may be used in conjunction with an x-ray system. For example, an electromagnetic tracking system may be used in conjunction with a C-arm fluoroscope. The C-arm fluoroscope may utilize an x-ray source at one end of the C-arm and an x-ray detector at the other end of the C-arm. The patient may be placed between the x-ray source and the x-ray detector. X-rays may pass from the x-ray source, through the patient, to the x-ray detector where an image is captured. The electromagnetic tracking system may generate an electromagnetic field between the ends of the C-arm and penetrate the body with minimal attenuation or change so tracking may continue during a surgical procedure.

One technique for generating the electromagnetic field involves using time-varying dipole fields. For example, dipole fields established by driving field-generating coils with an AC current signal. This approach allows synchronous demodulation of the induced signals and thus cumulate detected signal values to enhance sensitivity. Also, it allows the ability to establish the X, Y, and Z field components at different frequencies so that detected sensor output signals may be separated or demodulated simultaneously. This approach, however, has the disadvantage that varying magnetic fields induce eddy currents in the conductive structures found within the field. Induced currents themselves generate secondary magnetic fields, thus introducing distortions into the expected distribution. Conductive or ferromagnetic metal structures are generally commonly present in a medical tracking environment.

Once source of electromagnetic distortion in a C-arm environment is the x-ray detector. Historically, one technique to address the distortion from the x-ray detector is to mount a conducting structure about the x-ray detector. The conductor operates as a shield with respect to disturbances originating within the shield. The shield, which is typically structured as a metal can with openings at the top and bottom, then has a fixed position relative to one of the coil assemblies and may be effectively modeled. The eddy currents induced in the sheet metal cylinder by the magnetic field from the transmitter assembly, and the secondary field formed by these induced currents, may be modeled and accounted for in a distortion map.

Current shields, however, may allow signal leakage through seams, joints, and the x-ray detector window, for example. The signal leakage reduces the effectiveness of the shield. When the distortion map is created for calibration, it may take into account the signal leakage of the shield. In a situation in which a C-arm needs service or replacement parts, however, such parts may change the properties of the signal leakage (increase or decrease signal leakage, for example) through the shield. For example, if an image intensifier or flat panel detector is replaced, the properties of the signal leakage may be altered. If the properties of the signal leakage are altered, the distortion map may be mis-calibrated, resulting in improper operation of the tracking system.

The creation of the distortion map is typically performed using a robotics system during manufacturing and is a time consuming process. As the process for creating a distortion map is complicated and time consuming, it can be very costly in both monetary terms and in time, to perform on-site distortion mapping for calibration with new parts. Accordingly, a system and method is needed to minimize signal leakage from an electromagnetic shield. Such a system and method may minimize the need to recreate distortion maps, minimize equipment down time, and promote the interchangeability of replacement parts.

SUMMARY OF THE INVENTION

Certain embodiments of the present invention may include a system for an electromagnetic shield assembly for use with C-arms. The system may include a ring shield configured to encompass an x-ray detector. The ring shield may have a first window opening to receive x-rays. The system may include a window shield configured to shield the first window opening of the ring shield, wherein the window shield is electrically conductive and x-ray transparent. The ring shield may be electrically conductive, and either in electrical contact with the window shield or electrically insulated from the window shield. In an embodiment, the window shield may be aluminum or copper. The window shield may be integrated into an anti-scattering grid. The window shield may also include a high-magnetic permeability layer.

Certain embodiments of the present invention may include a system for an electromagnetic shield assembly for use with C-arms. The system may include a ring shield configured to encompass an x-ray detector. The ring shield may have a first window opening to receive x-rays. The system may include a window shield configured to shield the first window opening of the ring shield, wherein the window shield has a high-magnetic permeability and is x-ray transparent. The ring shield is electrically conductive and may be either in electrical contact with the window shield or may be electrically insulated from the window shield. The window shield may be integrated into an anti-scattering grid. In an embodiment, the window shield may be constructed of mu-metal or nickel. The window shield may also include an electrically conductive layer.

Certain embodiments of the present invention may include a system for a universal navigation target. The system may include a radiolucent calibration target. The system may also include an electromagnetic shield, wherein the electromagnetic shield includes a ring shield having a first window opening to receive x-rays and a window shield configured to shield the first window opening of the ring shield. The window shield may be electrically conductive and x-ray transparent. The window shield may have high-magnetic permeability and is x-ray transparent. The window shield may have high-magnetic permeability, be electrically conductive, and be x-ray transparent.

Figure 1:
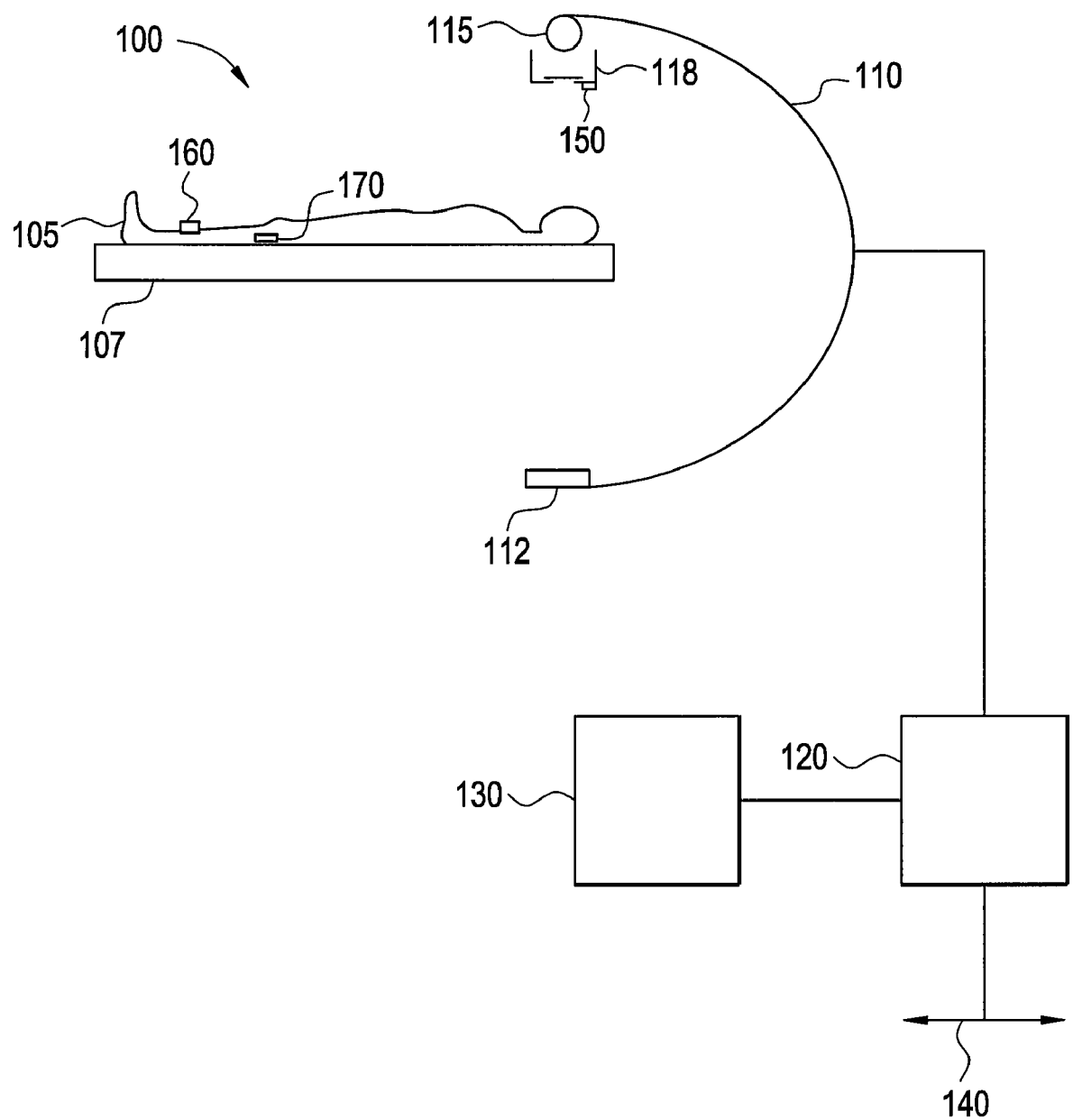
FIG. 1 illustrates a system that may be used for image guided surgery in accordance with an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

FIG. 1 illustrates a system 100 that may be used for image guided surgery in accordance with an embodiment of the present invention. The system 100 illustrates, as an example of a medical imaging unit, a C-arm unit 110. The medical imaging unit, however, may be other medical imaging equipment, such as an ultrasound unit, for example. Accordingly, any mobile medical imaging equipment may be used.

The C-arm unit 110 is connected to a computer unit 120. The connection between the C-arm unit 110 and the computer unit 120 may be wired or wireless. The computer unit 120 may be any equipment or software that permits electronic medical images, such as x-rays, ultrasound, CT, MRI, EBT, MR, or nuclear medicine for example, to be electronically acquired, stored, or transmitted for viewing and operation. The computer unit 120 may receive input from a user. The computer unit 120 represents, in general, equipment and software. The actual physical computer units may be separate units, part of a single unit, a computer system, or part of a computer system.

The computer unit 120 may be connected to other devices via an electronic network. The connection of the computer unit 120 to an electronic network is illustrated by line 140. The connection between the network 140 and the computer unit 120 may be wired or wireless. The computer unit 120 may also be connected to a display unit 130. The connection between the computer unit 120 and the display unit 130 may be wired or wireless. The display unit 130 may be a single display unit or multiple display units. Additionally, the display unit 130 may be a two-dimensional display unit or a three-dimensional display unit, for example. Accordingly, any display unit may be used in accordance with the present invention.

Element 105 represents a patient and element 107 represents a table on which the patient is lying. Elements 150, 160, and 170 are electronic sensors that may identify their location with reference to a reference frame and with reference to each other. Although three sensors 150-170 are shown, any number of sensors may be used. The sensors 150-170 are generally in electronic communication with the computer unit 120. Element 112 represents an x-ray source and element 115 represents an x-ray detector. The x-ray detector 115 may be, for example, an image intensifier or flat panel detector. Element 118 represents an electromagnetic shield. The electronic communication may be over a wire or may be transmitted in a wireless fashion. The components of the system 100 may be single units, separate units, may be integrated in various forms, and may be implemented in hardware and/or in software.

Figure 2:
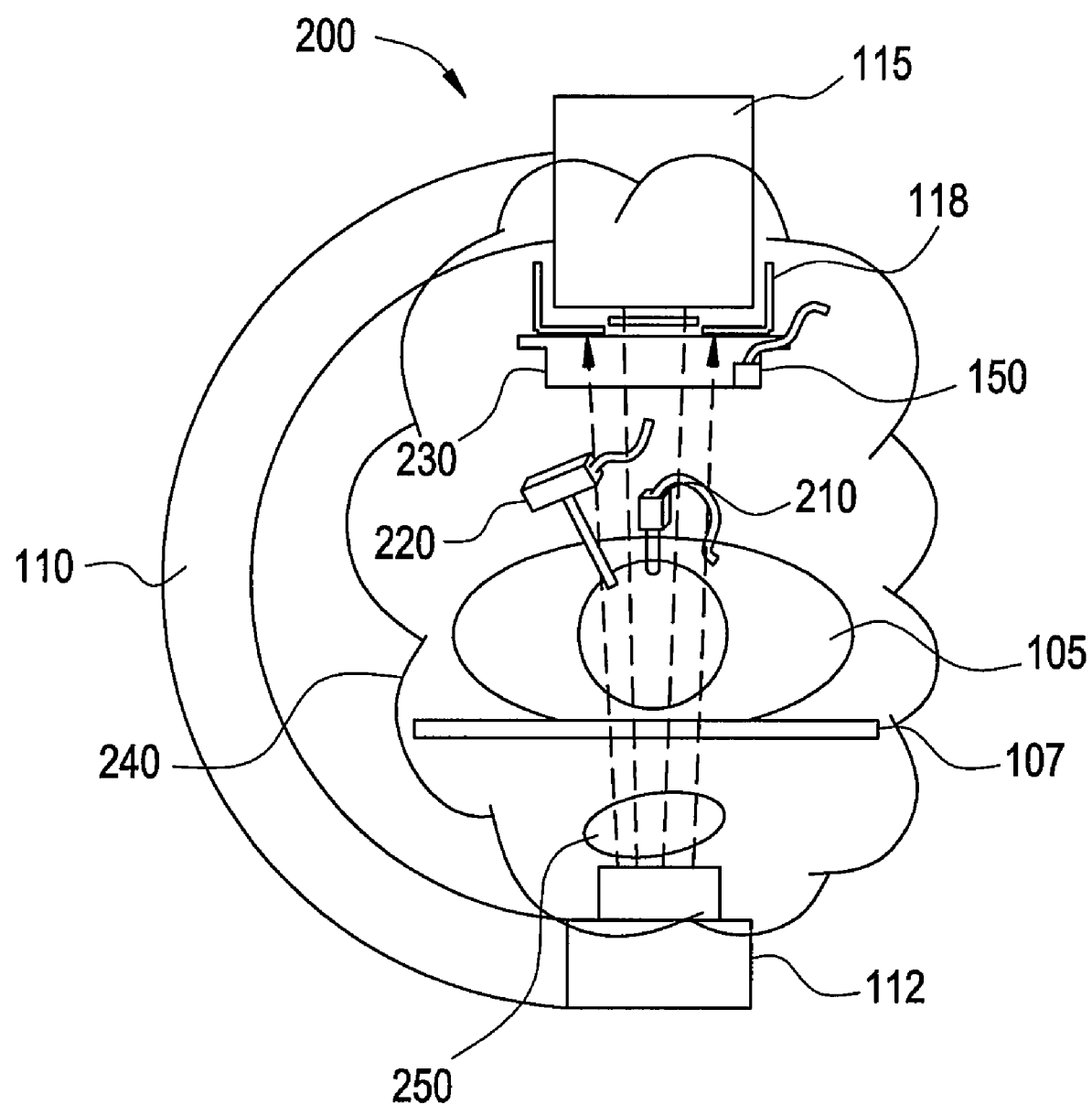
FIG. 2 illustrates a profile view of the system of FIG. 1 in accordance with an embodiment of the present invention.

FIG. 2 illustrates a system 200 that may be used for image guided surgery in accordance with an embodiment of the present invention. The system 200 is a profile view of the system 100. The C-arm 110, x-ray source 112, and x-ray detector 115 are shown. Also shown is the electromagnetic shield 118, sensor 150, the patient 105 and the table 107. In addition, a medical instrument 220, an electromagnetic transmitter 210, and a radiolucent calibration target 230 are shown. An electromagnetic field 240 is shown as are the x-rays 250. The medical instrument 220 may be connected to other medical equipment as is indicated by the wire attached to the medical instrument 220. The electromagnetic transmitter 210 may be connected to other equipment as is indicated by the wire attached to the electromagnetic transmitter 210.

In operation, the electromagnetic transmitter 210 creates the electromagnetic field 240 for the electromagnetic tracking system to track the medical instrument 220, for example. The electromagnetic field 240 may induce eddy currents in the conductive structures found within the electromagnetic field 240. For example, the electromagnetic field 240 may induce eddy currents in the x-ray detector 115. The induced currents may then generate secondary electromagnetic fields. The secondary electromagnetic fields may introduce distortions into the expected distribution.

The electromagnetic shield 118 may shield the sensors 150-170 from the secondary electromagnetic field. The electromagnetic shield 118 may include a conductive ring shield configured to encompass the x-ray detector 115. The conductive ring shield may encompass the x-ray detector 115 on the sides. In an embodiment, the conductive ring shield may slightly cover a portion of the bottom of the x-ray detector 115. Alternatively, the conductive ring shield may not cover the bottom of the x-ray detector 115. The conductive ring shield may have a window opening to allow x-rays 250 to reach the x-ray detector 115. The electromagnetic shield 118 may also include a conductive window shield. The conductive window shield is configured to shield the window opening of the conductive ring shield. In general, the conductive window shield is formed of a gage such that the x-rays 250 may pass through the conductive window shield with minimal x-ray attenuation.

Figure 3:
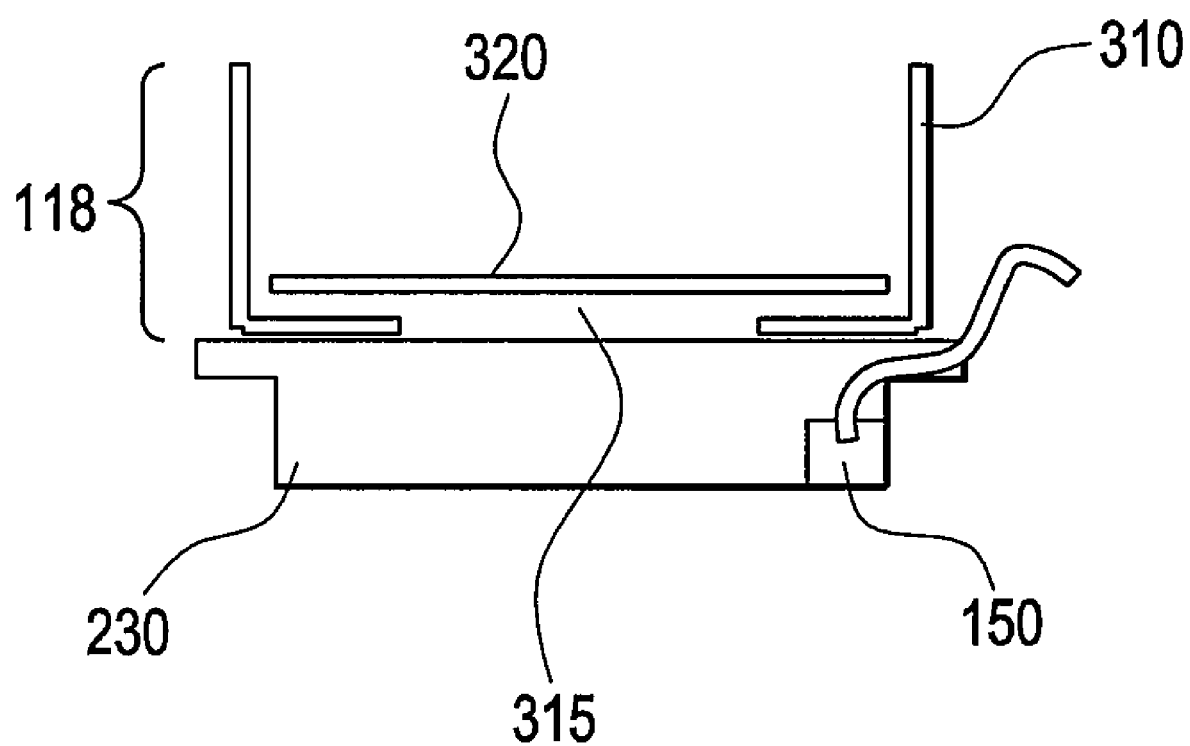
FIG. 3 illustrates an excerpt of FIG. 2 in accordance with an embodiment of the present invention.

FIG. 3 illustrates an excerpt of the system 200 in accordance with an embodiment of the present invention. FIG. 3 illustrates the radiolucent calibration target 230, the sensor 150 and the electromagnetic shield 118. The electromagnetic shield 118 includes the conductive ring shield 310 and the conductive window shield 320. The conductive ring shield 310 includes a window opening 315 for receiving x-rays 250 from the x-ray source 112 without minimal attenuation.

In general, the effectiveness of a shield may depend on the operating frequency and signal leakage through seams, joints, or holes. The signal leakage may reduce the shielding effectiveness. In the embodiment of FIG. 3, without the conductive window shield 320, signal leakage may occur though the window opening 315. For apertures on the shield with dimensions equal or less than half-wavelength, the shielding effectiveness in decibels is described by:

$$S = 20\log\left(\frac{\lambda}{2D}\right) \quad \text{Equation 1}$$

where λ is the wavelength, and D is the diameter of the aperture. As the size of the leakage hole increases, the shielding effectiveness drops accordingly. In an embodiment, it is desirable to have a conductive window shield 320 fully cover the window opening 315 for improving the total effectiveness of the shield. In one embodiment, the conductive ring shield 310 and the conductive window shield 320 may be electrically insulated from each other. In another embodiment, the conductive ring shield 310 and the conductive window shield 320 may be in electrical contact with each other.

In addition, the electrical properties and thickness of the shielding materials also affect the effectiveness of the shield. The effectiveness of a shielding material may be described by using the skin depth of the material:

$$\delta = \frac{1}{\sqrt{\pi f \mu \sigma}} \quad \text{Equation 2}$$

where $f$ is the operating frequency, μ and σ are permeability and conductivity of the shield, respectively. In general, thicker material may be used to shield low frequency signals to reach the same level of shielding attenuation. As the electromagnetic tracker signals are approximately 10 KHz, utilizing a conductive shield of approximately 3 mm thick aluminum may cause significant (approximately 20%) x-ray attenuation. This level of x-ray attenuation is generally unacceptable because it affects image quality.

The addition of the conductive window shield 320 improves the effectiveness of the electromagnetic shield 118 by allowing x-rays to pass through with minimal x-ray attenuation. For example, a conductive window shield 320 of thickness of 0.15 mm aluminum may introduce 0.1% attenuation to the x-ray image.

The conductive window shield 320 may be made of highly conductive materials such as aluminum and copper, or ferromagnetic material with high permeability such as mu-metal and nickel, or a combination thereof. As shown in Equation 2, both highly conductive and permeable materials may help increase the skin depth of a given shielding material. These materials may be used for attenuating signals with extremely high or low frequencies.

In another embodiment, the window shield 320 may be integrated to an anti-scattering x-ray grid. The anti-scattering x-ray grid may be installed in front of the x-ray detector. The anti-scattering x-ray grid is primarily used for removing the scattered radiation caused by various substances in the imaged subjects in order to produce sharp images. The anti-scattering x-ray grids are usually constructed by lead strips and aluminum interspaces with smooth, enameled aluminum or carbon fiber composite covers. Integrating the window shield 320 to the anti-scattering x-ray grid can provide rigid and durable structures for attaching the window shield 320 to the navigation target 230, as the window shield 320 may be constructed of thin conductive sheets or foils. A distortion map may be created for each integrated navigation target with the conductive ring shield 310 and conductive window shield 320 as well as the x-ray grid assemblies. The map may later be used for correcting the EM sensor position and orientation distortion during on-line image acquisition and instrument navigation.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A system for an electromagnetic shield assembly for use with C-arms, said system comprising:
    a radiolucent calibration target;
    a ring shield configured to encompass an x-ray detector, said ring shield having a first window opening to receive x-rays; and,
    a window shield configured to shield said first window opening of said ring shield, wherein said window shield is electrically conductive and x-ray transparent.

2. The system of claim 1, wherein said ring shield is electrically conductive.

3. The system of claim 1, wherein said ring shield is in electrical contact with said window shield.

4. The system of claim 1, wherein said ring shield is electrically insulated from said window shield.

5. The system of claim 1, wherein said window shield is integrated into an anti-scattering grid.

6. The system of claim 1, wherein said window shield is constructed of aluminum.

7. The system of claim 1, wherein said window shield is constructed of copper.

8. The system of claim 1, wherein the window shield further comprises a high-magnetic permeability layer.

9. A system for an electromagnetic shield assembly for use with C-arms, said system comprising:
    a radiolucent calibration target;
    a ring shield configured to encompass an x-ray detector, said ring shield having a first window opening to receive x-rays; and,
    a window shield configured to shield said first window opening of said ring shield, wherein said window shield has a high-magnetic permeability and is x-ray transparent.

10. The system of claim 9, wherein said ring shield is electrically conductive.

11. The system of claim 9, wherein said ring shield is in electrical contact with said window shield.

12. The system of claim 9, wherein said ring shield is electrically insulated from said window shield.

13. The system of claim 9, wherein said window shield is integrated into an anti-scattering grid.

14. The system of claim 9, wherein said window shield is constructed of mu-metal.

15. The system of claim 9, wherein said window shield is constructed of nickel.

16. The system of claim 9, wherein the window shield further comprises an electrically conductive layer.

17. A system for a universal navigation target, said system comprising:
    a radiolucent calibration target;
    an electromagnetic shield, wherein said electromagnetic shield includes a ring shield having a first window opening to receive x-rays and a window shield configured to shield said first window opening of said ring shield.

18. The system of claim 17, wherein said window shield is electrically conductive and x-ray transparent.

19. The system of claim 17, wherein said window shield has a high-magnetic permeability and is x-ray transparent.

20. The system of claim 17, wherein said window shield has a high-magnetic permeability, is electrically conductive, and is x-ray transparent.

* * * * *